United States Patent [19]

Schaefer

[11] 4,442,536

[45] Apr. 10, 1984

[54] X-RAY EXAMINATION APPARATUS

[75] Inventor: Willi Schaefer, Erlangen, Fed. Rep. of Germany

[73] Assignee: Siemens Aktiengesellschaft, Berlin & Munich, Fed. Rep. of Germany

[21] Appl. No.: 284,101

[22] Filed: Jul. 16, 1981

[30] Foreign Application Priority Data

Aug. 11, 1980 [DE] Fed. Rep. of Germany ....... 3030379

[51] Int. Cl.³ ............................................. G03B 41/16
[52] U.S. Cl. ......................................... 378/26; 378/27
[58] Field of Search ....................... 378/26, 27, 25, 21

[56] References Cited

U.S. PATENT DOCUMENTS 4,315,156  2/1982  Sell ........................................ 378/26
4,335,312  6/1982  Onken .................................... 378/26

FOREIGN PATENT DOCUMENTS 2311310  9/1974  Fed. Rep. of Germany .

*Primary Examiner*—Craig E. Church

*Attorney, Agent, or Firm*—Hill, Van Santen, Steadman & Simpson

[57] ABSTRACT

In an exemplary embodiment, an x-ray tube is mounted on a tube support arm carried on a separate tube stand. A layer rod releasably couples with the tube support arm for the purpose of aligning the x-ray tube relative to a displaceable radiographic installation on the underside of the patient support platform. The tube need not always be aligned relative to such radiographic installation, but may be aligned, according to requirements, relative to a second radiographic installation. In order to facilitate such change of alignment, the disclosure provides that the layer rod may be placed in a loosely coupled state relative to the tube support arm, and that it bears coupling surfaces which are capable of being brought into positive locking engagement with the tube support arm to effect automatic reorientation of the x-ray tube (without prior manual alignment of the x-ray tube to the radiographic installation) during recoupling operation. The x-ray examination apparatus is particularly suited for utilization in the case of diagnostic x-ray examination apparatus.

18 Claims, 5 Drawing Figures

X-RAY EXAMINATION APPARATUS

BACKGROUND OF THE INVENTION

The invention relates to an x-ray examination apparatus comprising a patient support platform, a tube stand which is movable parallel to the longitudinal axis of the horizontally positioned patient support platform, an x-ray tube which is mounted in overlying relation to the patient support platform on a tube support arm carried by the tube stand, a radiographic installation which is shiftable longitudinally of the patient support platform at an opposite side of the patient support platform from the x-ray tube, and a so-called layer rod for selective coupling engagement with the tube support arm so as to maintain alignment of the x-ray tube with the radiographic installation during a laminographic scanning operation.

In physicians' offices and smaller x-ray departments x-ray examination apparatus is frequently encountered in which the x-ray tube is mounted on a separate tube stand shiftable parallel to the longitudinal axis of the patient support platform. It is selectably usable in conjunction with a radiographic installation which is longitudinally displaceable beneath the patient support platform, such as e.g., a Bucky diaphragm or, following rotation of the tube support arm, in conjunction with an entirely different radiographic installation, such as, for example, a screen of a wall-type x-ray apparatus. For the centering of the cone of rays of the x-ray tube relative to the radiographic installation, shiftable beneath the patient support platform, it is generally conventional to provide a centering rod—also called a layer rod on account of the general utilization in the case of layer scanning (laminographic) apparatus—which, at its one end, is in engagement with the radiographic installation, and, at its other end, with the tube support arm. If, in the case of such an x-ray examination apparatus, centering relative to the radiographic installation is no longer desired, because, for example, one wishes to operate with the screen of a wall-type x-ray apparatus, an operating individual must uncouple the layer rod from the tube support arm and align the x-ray tube relative to the other radiographic installation, and vice versa.

Through the German Offenlegungsschrift 23 11 310 an x-ray examination apparatus comprising an overtable x-ray tube is known which is mounted on a tube tower drivable along the table frame. In the case of this x-ray examination apparatus, there is disposed, in the table frame, adjacent to one another, an x-ray spot film apparatus with an image intensifier television installation and a sheet film changer. Here, also, the x-ray spot film apparatus is connected by a layer rod with the tube support arm. The layer rod keeps the x-ray tube always aligned to the image layer (film) of the x-ray spot film apparatus, even in the case of oblique radiographs. If, in the case of this x-ray examination apparatus, operation is to be carried out with the sheet film changer, then the x-ray tube must be uncoupled from the layer rod and coupled with the tube tower which is always perpendicularly aligned, in order to align the path of rays perpendicularly to the patient support platform. For this purpose, an electromagnetic drive and a mechanical coupling installation are disclosed. It is a peculiar feature of this x-ray examination apparatus that, in the case of the electromagnetic as well as in the case of the mechanical design, this recoupling can be carried out only in the position of the x-ray tube in which the layer rod and the tube tower are aligned exactly parallel to one another. Also, in the case of the mechanical design, during the transition from the examination operation with the x-ray spot film apparatus to the radiography operation with the sheet film changer, the operator must always walk around the patient support platform in order to shift the clutch disk.

SUMMARY OF THE INVENTION

The object underlying the invention resides in finding as simple as possible an apparatus for the coupling of the x-ray tube with the layer rod. This coupling device should also be operable in the case of simple hand-adjusted apparatus parts, in which no exact initial position of the tube stand; i.e., no exact parallel position of the layer rod to the tube stand, is guaranteed. In addition, the coupling operation should always be capable of being executed from the operating side; i.e., without an operator having to walk around the x-ray examination apparatus.

In the case of an x-ray examination apparatus of the type initially cited, accordingly, a layer rod is longitudinally displaceable on the radiographic installation as well as on the tube support arm, and bears, in the case of longitudinal displacement, guide surfaces capable of being brought into engagement with the tube support arm in a positive locking fashion. This construction renders superfluous a detachment of the layer rod from the tube support arm or from the radiographic installation. Even in the uncoupled state, the layer rod always remains connected with the tube support arm and the radiographic installation. Thus, a precondition is provided in order to be able to carry out the coupling virtually from each initial position. For this purpose, an additional degree of freedom—the longitudinal displacement—of the layer rod is utilized.

Particularly great torques can be transmitted if the layer rod, in an embodiment of the invention, is provided with shoulders capable of being brought to rest against correspondingly matched guide surfaces of the tube support arm. This is particularly of significance if the tube support arm and layer rod, during the coupling operation, are not aligned relative to one another, and the coupling operation itself must effect a relative rotation of the tube support arm with respect to the layer rod.

In a particularly expedient further development of the invention, a wedge-shaped guide surface—in engagement with a counter surface of the layer rod—of a control element can be displaceable on the tube support arm transversely to the longitudinal axis of the layer rod. This construction manages with simple mechanical structural parts. It can also be serviced and repaired at any time in newly developing countries with the simple tools available there. In addition, such a coupling is capable of actuation in each pivot position of the layer rod relative to the tube support arm, and simultaneously guarantees a connection which is free from play.

The operation of the x-ray examination apparatus is particularly facilitated if a positioning element for the control element, in an embodiment of the invention, is arranged next to the handle mounted on the x-ray tube, on the side of the x-ray tube not facing the layer rod. It is hereby achieved that the operating individual, during re-coupling, can remain at his work place. Thus, he is spared the cumbersome path around the patient support platform to the tube stand.

Further details of the invention shall be explained on the basis of several exemplary embodiments illustrated in the figures of the accompanying drawing sheets; and other objects, features and advantages will be apparent from this detailed disclosure and from the appended claims.

DETAILED DESCRIPTION

Figure 1:
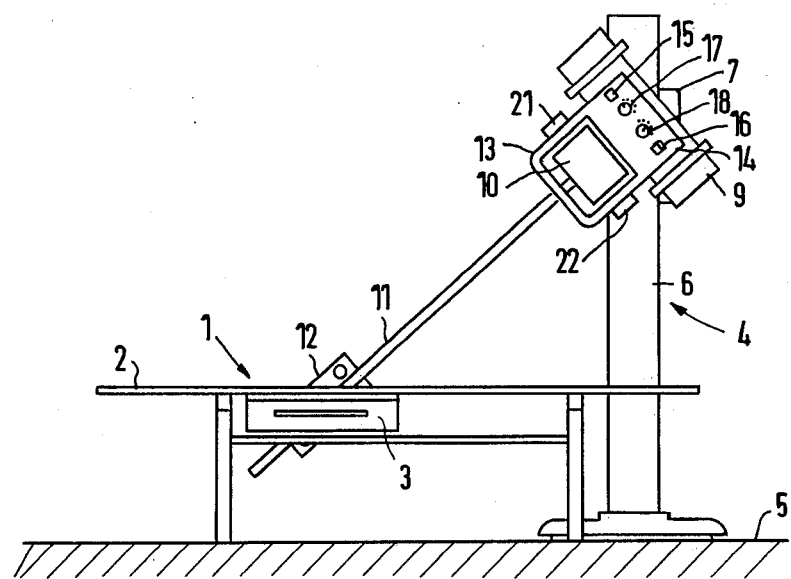
FIG. 1 illustrates a schematic view of an x-ray examination apparatus comprising an x-ray tube support-mounted on a separate tube stand.

In FIG. 1, one recognizes an examination table 1 with a horizontal patient support platform 2 and a Bucky diaphragm 3 displaceably mounted in the examination table directly beneath the patient support platform, and movable along the length of the same. Next to the examination table there is a tube stand 4 which is capable of being driven parallel to the longitudinal axis of the patient support platform 2 on the floor 5. The tube stand 4, on a stand carriage 7 which is height-adjustable along the length of the pillar (or upright) 6, supports an x-ray tube 9 which is pivotal about a horizontal axis 8 (FIG. 2), with a flange-mounted x-ray diaphragm 10. The x-ray tube 9 and the Bucky diaphragm 3 are interconnected via a so-called layer rod 11. The latter is longitudinally displaceably mounted, on a pivotal roller bearing 12, on the Bucky diaphragm 3 on the rear side of the examination table 1 in the illustration of FIG. 1. On the side facing the viewer, the x-ray tube 9 supports a grab handle 13 (FIG. 2), designed in the form of a stirrup piece, and, above the stirrup piece, an operating box 14. On this operating box 14 there are arranged the switching key 15 for the locking of the longitudinal displacement of the tube stand 4 and of the height-adjustment of the stand carriage 7, as well as the switching key 16 for the locking of the rotation of the x-ray tube 9 about the horizontal axis 8 by means of magnetic brakes (not illustrated). Between these two switching keys there are disposed adjusting knobs 17, 18, for the adjustment of the x-ray diaphragm 10.

Figure 2:
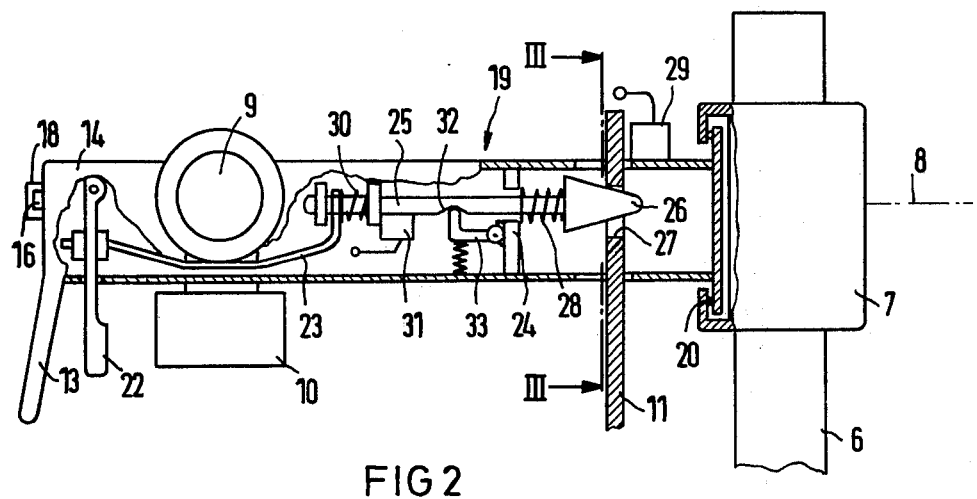
FIG. 2 illustrates a partially opened-up representation of the tube support arm.

In FIG. 2 details of the construction of the tube support arm 19 can be recognized. On the stand carriage 7, which is height-adjustable along the pillar 6 of the tube stand 4, the tube support arm 19 is rotatably mounted about its longitudinal axis by means of a rotary bearing 20. The x-ray tube 9 is rigidly mounted on the tube support arm 19. In front of the radiation exit side of the x-ray tube 9, the x-ray diaphragm 10 is flanged-mounted. The operating box 14, arranged on the side of the x-ray tube 9 remote from the pillar 6, and including the switching keys 15, 16, and adjusting knobs 17, 18, is, as FIG. 2 shows, an integrated component part of the tube support arm 19. Immediately behind the U-shaped stirrup piece 13, parallel to its two legs, one grip section 21, 22, each is pivotally mounted in the operating box.

These grip sections are, via an auxiliary rod 23 (only one visible), connected with a control rod 25 which is axially displaceable in the tube support arm 19 and guided at a bearing location 24. This control rod carries, at its free end, a conical pin 26 which, in the illustration of FIG. 2, is inserted in a bore 27 introduced in the layer rod 11. The bore 27 of the layer rod 11 is so dimensioned in its diameter that the conical pin 26 of the control rod can be pushed through even with its large diameter. The control rod 25 bears, between the conical pin 26 and its bearing location 24 in the tube support arm 19, a spring 28 resting against the bearing location and pressing the pin into the bore 27.

On the tube support arm 19 a cam-operated switch 29 is mounted which, in the upper extreme position of the layer rod 11 in which the pin 26 is almost entirely inserted into the bore 27 of the layer rod, is actuated by said layer rod. The auxiliary rods 23 are coupled to the control rod 25 jointly with a short play. This play is accommodated by a spring 30, encircling the control rod, which spring 30 presses the control rod 25 into the bore 27 of the layer rod 11. The relative movement between the auxiliary rods 23 and the control rod 25 is sensed by a cam operated switch 31, mounted on the control rod 25, releasing the magnetic brakes in the case of actuation. The control rod 25, in addition, possesses an indentation 32 which, in the operating position of the control rod 25, in which the pin 26 with its thin tip is just inserted into the bore 27 of the layer rod, is capable of being brought in engagement with a spring-loaded detent latch 33 installed in the housing of the tube support arm 19.

Figure 3:
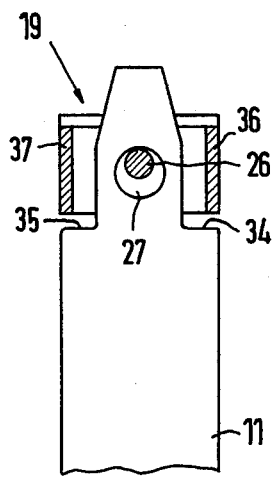
FIG. 3 illustrates a section taken along the line III—III of FIG. 2.

FIG. 3 illustrates the guidance of the layer rod 11 on the tube support arm 19. The layer rod 11 projects, with its upper tapered end, into the tube support arm 19. It is tapered in step-fashion on its end projecting into the tube support arm 19, so that two shoulders 34, 35 form at the transition to the tapered portion. The width of the layer rod is so selected that the shoulders extend beneath the wall portions 36, 37, of the rectangular tube support arm 19. The tapered portion of the layer rod 11, moreover, is so narrowly dimensioned that, on the one hand, it does not obstruct the operational pivoting of the layer rod 11 relative to the tube support arm 19 and, on the other hand, still can accommodate the bore 27.

Figure 4:
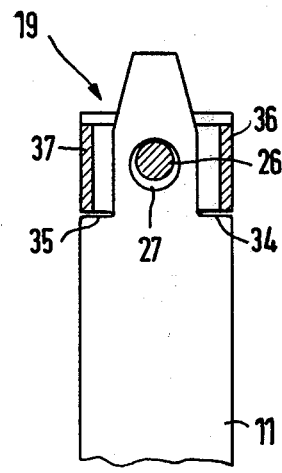
FIG. 4 illustrates the representation of FIG. 3, however with a layer rod which is rigidly coupled on the tube support arm.

FIG. 4 shows the same illustration as FIG. 3, whereby, however, the pin 26 is inserted as deeply as possible into the bore 27 of the layer rod 11. In this operating position, the layer rod 11 is so strongly raised by the pin relative to the tube support arm 19 that it rests with its shoulders 34, 35, against the housing of the tube support arm. It holds the tube support arm 19 aligned to the layer rod 11 and simultaneously prevents a deeper insertion of the pin in the bore 27.

The examining physician, if he grasps the retaining stirrup piece 13 and releases the electromagnetic brakes with the switching keys 15, 16 on the control box 14 of the x-ray tube 9, can shift the x-ray tube along the examining table 1 and also in height. The tube stand 4 is thus entrained in table longitudinal direction and the support arm 19 with the stand carriage 7 is shifted along the pillar 6. These movements are not obstructed by the layer rod 11, which is guided on the pivotal roller bearing 12 of the Bucky diaphragm 3 in a longitudinally displaceable fashion. The layer rod 11 is here supported by the pin 26 which extends through the bore 27. If, as is illustrated in FIGS. 2 and 3, the shoulders 34 and 35 of the layer rod 11 do not rest against the wall parts 36, 37 of the tube support arm 19, then, in the range of the normal adjustment of the x-ray tube 9, also no obstruction of the rotation of the tube support arm 19 by the layer rod 11 occurs.

If, however, the x-ray tube 9 with the x-ray diaphragm 10 is to be aligned relative to the Bucky diaphragm 3, then the physician need only push with his fingers the rear grip sections 21, 22, away from the retaining stirrup piece 13 of the x-ray tube 9. Thus, initially the spring 30 is compressed and the cam-operated switch 31 is actuated. The cam-operated switch 31 releases the magnetic brakes which release the rotational movement of the tube support arm 19 about its longitudinal axis. In the case of a stronger pushing away of the grip sections 21, 22, the control rod 25, mounted in the tube support arm 19 in a longitudinally displaceable fashion, is displaced by the auxiliary rod 23, in the illustration according to FIG. 2, toward the right, whereby the pin 26 is pressed into the bore 27 of the layer rod 11. This movement is reinforced by the spring 28. Simultaneously the layer rod 11 is drawn up by the pin 26, counter to its own weight, until the shoulders 34, 35, of the layer rod are pressed against the lower edge of the rectangular tube support arm 19 as shown in FIG. 4. In this position, the tube support arm 19 is connected with the layer rod 11 free from play; namely, such that the central ray of the x-ray tube is aligned parallel to the layer rod, and hence also aligned with the Bucky diaphragm. The control rod 25 is retained by the spring 28 in this position. Through the cam-operated switch 29 the coupling of the layer rod 11 with the tube support arm 19 is sensed. The completed coupling can thus be displayed on the operating console (not illustrated) of the x-ray examination apparatus.

If, by contrast, the x-ray tube is to be employed in conjunction with a different radiographic installation, for example, a screen of a wall apparatus standing next to the examination table (not illustrated), then the x-ray support arm 19 can also be completely uncoupled from the layer rod. For this purpose, the grip sections 21, 22, need only be completely drawn toward the retaining stirrup piece 13 of the tube support arm 19. The pin 26 is thus entirely withdrawn from the bore 27 of the layer rod 11 via the auxiliary rods 23 and the control rod 25. The layer rod 11, guided through the roller bearing 12 of the Bucky diaphragm 3, slides downwardly until it stands on the floor or on a support-mounting provided for this purpose (not illustrated). Now, the pillar 4 with the tube support arm 19 and the x-ray tube 9 can be completely freely moved, and the x-ray tube, through rotation as desired about the axis 8 of the tube support arm 19 and height adjustment of the stand carriage 7, can be aligned with the examination region of the other radiographic installation. This complete uncoupling of the layer rod 11 provides the possibility, with a single x-ray tube support-mounted on a tube stand 4, of being able to operate several work places, or x-ray examination apparatus, respectively.

Figure 5:
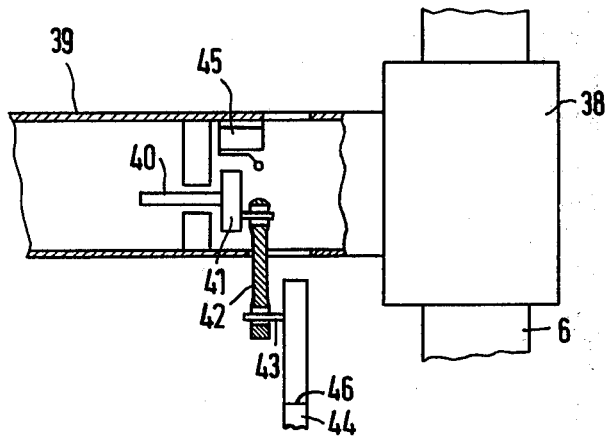
FIG. 5 illustrates another tube support arm with a layer rod capable of being coupled via an eccentric.

FIG. 5 illustrates another tube support arm 39 rotatably mounted on a stand carriage 38 which, instead of a control rod, supports a control shaft 40 with an eccentric 41. A crank arm 42 is rotatably mounted on the eccentric 41, which crank arm, in turn, is rotatably mounted on a bolt 43 of the layer rod 44.

The position of the crank arm 42 is monitored by a cam-operated switch 45. The layer rod 44, similarly to the layer rod 11, has two shoulders (46) (only one visible).

If the layer rod 44 is to be coupled with the tube support arm 39, then the control shaft 40 with the eccentric 41 must be rotated approximately 180° in relation to the illustration of FIG. 5. The crank arm 42 thus pulls up the layer rod 44 on the bolt 43 until the shoulders 46 of the layer rod, like in the illustration of FIGS. 3 and 4, rest against the lower edge of the tube support arm 39 and prevent a further rotation of the eccentric 41. This position of the layer rod 44 is sensed by the cam-operated switch 45 and can be displayed by the latter on the operating console (not illustrated) of the x-ray examination apparatus. The illustration of FIG. 5 shows the layer rod in the noncoupled state. It is noticeable here that the layer rod 44 in this position no longer projects into the tube support arm 39, such as was still the case in the exemplary embodiment of FIGS. 2, 3, and 4. This provides the particular advantage that the layer rod 44, in the noncoupled state, can be pivoted about the bolt 43 by more than 90°. This enlarged pivoting capability—in comparison to the exemplary embodiment of FIGS. 2 and 3—of the noncoupled layer rod provides the great advantage that the layer rod need not be detached from the tube support arm even when one intends to pivot the tube support arm through 90°, for example, in order to operate, with the x-ray tube, a different radiographic device, for example, a wall-type x-ray apparatus.

It is a great advantage of the illustrated constructions that they render unnecessary a precise alignment of the x-ray tube to the layer rod prior to the coupling operation. The precision aignment prior to coupling of the layer rod to the x-ray tube can be dispensed with since the tube support arm is automatically oriented relative to the layer rod during the coupling operation. Thus the x-ray tube is automatically aligned with the film carrier 3 (image recording means), regardless of the angular disposition of the layer rod (coupling rod) at the time that coupling is effected. Precisely in the case of simple, hand-operated apparatus, such a previous precise alignment of the tube support arm relative to the layer rod is not readily possible. In addition, it turns out to be favorable that this construction is sturdy and manages with mechanical component parts which can be readily serviced and subsequently worked even in newly developing countries. It would also be possible, instead of with shoulders, to draw-in the layer rod, so that conically bevelled flanks (or edges) of the layer rod snugly engages conforming guide walls of an aperture in the tube support arm. However, such a construction would require greater heights of lift in longitudinal direction of the layer rod than in the case of the illustrated exemplary embodiments.

It will be apparent that many modifications and variations may be effected without departing from the scope of the novel concepts and teachings of the present invention.

I claim as my invention:

1. An x-ray examination apparatus comprising a patient support platform, a tube stand displaceable parallel to the longitudinal axis of the horizontally positioned patient support platform, a tube support arm mounted by the tube stand, an x-ray tube support-mounted on the tube support arm on one side of the patient support platform, and a radiographic installation having an image recording means displaceable along the patient support platform at an opposite side of the patient support platform, said radiographic installation having a coupling rod capable of being coupled with the tube support arm for aligning the x-ray tube relative to the image recording means, characterized in the coupling rod being longitudinally displaceable at the image recording means and being longitudinally shiftable relative to the tube support arm and having surfaces longitudinally movable with the coupling rod so as to be moved into positive locking engagement with the tube support arm, said coupling rod having a first end connected with said tube support arm and having a second end coupled directly with said image recording means and rigidly connected with said first end, said first end of said coupling rod in a first mode of operation having said surfaces thereof in said positive locking engagement with said tube support arm such that pivotal movement of said tube support arm causes conjoint swinging movement of the first and second ends of said coupling rod without change in the length of said coupling rod, the second end of said coupling rod moving longitudinally relative to the image recording means as the image recording means moves along the patient support platform, and said coupling rod being shiftable as a unit in the longitudinal direction thereof to move said surfaces out of positive locking engagement with the tube support arm to allow pivotal movement of the tube support arm in a second mode of operation without requiring a corresponding swinging movement of said coupling rod and without requiring complete disconnection of the first end of the coupling rod from the tube support arm.

2. An x-ray examination apparatus according to claim 1, characterized in that the coupling rod is provided with shoulders providing said surfaces, and means for pressing said shoulders against cooperating surfaces of the tube support arm to maintain said positive locking engagement during said pivotal movement of said tube support arm in said first mode of operation.

3. An x-ray examination apparatus according to claim 1, characterized in that an eccentric, rotatably mounted on the tube support arm, is coupled with the coupling rod for holding the coupling rod surfaces in positive locking engagement with the tube support arm in one angular position thereof, and for shifting the coupling rod to allow independent pivotal movement of the tube support arm without complete disconnection of the coupling rod from the tube support arm.

4. An x-ray examination apparatus according to claim 1, characterized by coupling means having a stable operating condition corresponding to said second mode of operation wherein the coupling rod is only loosely coupled with the tube support arm.

5. An x-ray examination apparatus according to claim 1, with a handle for the adjustment of the x-ray tube, characterized in that control means for controlling the locking engagement of the coupling rod with the tube support arm is manually actuated adjacent the handle.

6. An x-ray examination apparatus according to claim 1, characterized in a cam-operated switch for sensing the complete locking engagement of the coupling rod with the tube support arm.

7. An x-ray examination apparatus according to claim 1, characterized in control means for longitudinally shifting said coupling rod relative to said support arm, said control means comprising a control element having a wedge-shaped guide surface, the first end of the coupling rod having a counter surface for engagement with the wedge-shaped guide surface, and the control element being displaceable on the tube support arm transversely to the longitudinal axis of the coupling rod to shift said coupling rod longitudinally so as to bring the surfaces of the coupling rod into said positive locking engagement with the tube support arm.

8. An x-ray examination apparatus according to claim 7, with a handle mounted with the x-ray tube on the side of the x-ray tube remote from the coupling rod, characterized in a positioning element arranged next to the handle and being manually movable for actuating the control element.

9. An x-ray examination apparatus according to claim 7, characterized in that holding means are associated with the control element which selectively hold it in a first position where the coupling rod is connected with but rotatable relative to the tube support arm, and in a second position where the coupling rod is in positive locking engagement with the tube support arm so as to require joint rotation thereof.

10. An x-ray examination apparatus according to claim 7, characterized in that the coupling rod can be completely removed from the tube support arm by means of a complete removal of the wedge-shaped guide surface from the coupling rod counter surface.

11. An x-ray examination apparatus comprising a patient support platform, a tube stand displaceable parallel to the longitudinal axis of the horizontally positioned patient support platform, a tube support arm mounted by the tube stand, an x-ray tube support-mounted on the tube support arm on one side of the patient support platform, and a radiographic installation having an image recording means displaceable along the patient support platform at an opposite side of the patient support platform, said radiographic installation having a coupling rod capable of being coupled with the tube support arm for aligning the x-ray tube relative to the image recording means, characterized in the coupling rod being longitudinally displaceable at the image recording means and being longitudinally shiftable relative to the tube support arm and having surfaces longitudinally movable with the coupling rod so as to be moved into positive locking engagement with the tube support arm, said coupling rod having a first end connected with said tube support arm and having a second end coupled with said image recording means and connected with said first end, said first end of said coupling rod in a first mode of operation having said surfaces thereof in said positive locking engagement with said tube support arm such that pivotal movement of said tube support arm causes conjoint swinging movement of the first and second ends of said coupling rod, the second end of said coupling rod moving longitudinally relative to the image recording means as the image recording means moves along the patient support platform, and control means carried by said tube support arm and in one operating condition holding said surfaces of said coupling rod in positive locking engagement with the tube support arm and in a second operating condition only loosely holding said coupling rod against disconnection from the tube support arm, with said surfaces spaced from said tube support arm to allow pivotal movement of the tube support arm in a second mode of operation without requiring a corresponding swinging movement of said coupling rod and without requiring complete disconnection of the first end of the coupling rod from the tube support arm.

12. An x-ray examination apparatus according to claim 11, characterized in that said control means comprises an eccentric, rotatably mounted on the tube support arm, and coupled with the coupling rod for holding the coupling rod surfaces in positive locking engagement with the tube support arm in one angular position thereof, and for shifting the coupling rod to allow independent pivotal movement of the tube support arm without complete disconnection of the coupling rod from the tube support arm.

13. An x-ray examination apparatus according to claim 11, characterized by said control means having a means establishing a stable operating condition corresponding to said second mode of operation wherein the coupling rod is only loosely coupled with the tube support arm.

14. An x-ray examination apparatus according to claim 11, with a handle for the adjustment of the x-ray tube, characterized in that said control means for controlling the locking engagement of the coupling rod with the tube support arm is manually actuated adjacent the handle.

15. An x-ray examination apparatus according to claim 11, characterized in that the coupling rod is provided with shoulders providing said surfaces, said control means pressing said shoulders against cooperating surfaces of the tube support arm to maintain said positive locking engagement during said pivotal movement of said tube support arm in said first mode of operation.

16. An x-ray examination apparatus according to claim 15, characterized in said control means comprising a control element having a wedge-shaped guide surface, the first end of the coupling rod having a counter surface for engagement with the wedge-shaped guide surface, and the control element being displaceable on the tube support arm transversely to the longitudinal axis of the coupling rod to shift said coupling rod longitudinally so as to bring the shoulders of the coupling rod into said positive locking engagement with the tube support arm.

17. An x-ray examination apparatus according to claim 16, with a handle mounted with the x-ray tube on the side of the x-ray tube remote from the coupling rod, characterized in a positioning element arranged next to the handle and being manually movable for actuating the control element.

18. An x-ray examination apparatus according to claim 16, characterized in that holding means are associated with the control element which selectively hold it in a first position where the coupling rod is connected with but rotatable relative to the tube support arm, and in a second position where the coupling rod is in positive locking engagement with the tube support arm so as to require joint rotation thereof.

* * * * *